United States Patent [19]

Konno et al.

[11] Patent Number: 4,879,119

[45] Date of Patent: * Nov. 7, 1989

[54] PATCH

[75] Inventors: Yutaka Konno; Hiroitsu Kawata; Masayoshi Aruga; Takashi Sonobe, all of Saitama; Mitsuo Mitomi, Tokyo, all of Japan

[73] Assignee: Yamanouchi Pharmaceutical Co., Ltd., Tokyo, Japan

[ * ] Notice: The portion of the term of this patent subsequent to Aug. 11, 2004 has been disclaimed.

[21] Appl. No.: 239,013

[22] Filed: Aug. 26, 1988

Related U.S. Application Data

[63] Continuation of Ser. No. 17,886, Feb. 20, 1987, abandoned, which is a continuation of Ser. No. 699,585, Feb. 8, 1985, Pat. No. 4,685,911.

[30] Foreign Application Priority Data

Feb. 21, 1984 [JP] Japan ................................. 59-31934

[51] Int. Cl.$^4$ ............................................. A61F 13/00
[52] U.S. Cl. ................................... 424/449; 424/448
[58] Field of Search ................................ 424/449, 448

[56] References Cited

U.S. PATENT DOCUMENTS

| | | | |
|---|---|---|---|
| 2,055,063 | 9/1936 | Bird | 514/786 |
| 3,122,475 | 2/1964 | Shaeppi | 424/436 |
| 3,415,249 | 12/1968 | Sperti | 424/436 |
| 3,485,847 | 12/1969 | Bossert et al. | 514/356 |
| 3,821,372 | 6/1974 | Vanlerberghe et al. | 514/786 |
| 4,230,105 | 10/1980 | Harwood | 128/156 |
| 4,344,968 | 8/1982 | Aoda et al. | 424/436 |
| 4,401,664 | 8/1983 | Scheuffger | 514/786 |
| 4,455,146 | 6/1984 | Noda et al. | 424/448 |
| 4,462,984 | 7/1984 | Mizuno et al. | 514/786 |
| 4,555,524 | 11/1985 | Gruber et al. | 514/786 |
| 4,572,832 | 2/1986 | Kigasawa | 424/435 |
| 4,585,452 | 4/1986 | Sablotsky | 604/892 |
| 4,637,930 | 1/1987 | Konno et al. | 424/449 |
| 4,685,911 | 8/1987 | Konno et al. | 604/897 |

FOREIGN PATENT DOCUMENTS

| | | | |
|---|---|---|---|
| 0052216 | 3/1983 | Japan | 424/449 |
| 0055417 | 4/1983 | Japan | 424/445 |

Primary Examiner—Thurman K. Page
Assistant Examiner—Leon R. Horne
Attorney, Agent, or Firm—Burgess, Ryan & Wayne

[57] ABSTRACT

A patch having good transdermal property which utilizes a suppository base e.g. triglyceride of a vegetable saturated fatty acid having 12 to 18 carbon atoms together with a penetration enhancer.

7 Claims, 1 Drawing Sheet ved, which is a continu-
PATCH

This is a continuation of application Ser. No. 17,886, filed Feb. 20, 1987, now abandoned, which is a continuation of application Ser. No. 699,585, filed Feb. 8, 1985.

FIELD OF THE INVENTION

This invention relates to a patch and more particularly to a patch showing an increased skin penetration rate of drug and an increased drug releasing rate.

BACKGROUND OF THE INVENTION

A patch is one form of transdermal formulations whose application for systemic therapy is recently in the limelight and has hitherto been applied to nitroglycerin, scopolamine, etc.

Among these patches, the patches known as the patch of nitroglycerin are one containing a crosslinked silicon polymer as a base, one containing a viscous silicone liquid as a base together with multi-pore membrane for controlled release of drug, and one containing a matrix composed of polyvinyl alcohol, polyvinyl pyrrolidone, and glycerol as a base. Also, the patch of scopolamine contains a mixture of high molecular polyisobutene, low molecular polyisobutene, and a mineral oil as a base.

SUMMARY OF THE INVENTION

On the other hand, this invention provides a patch having good transdermal property by using a suppository base which has never been used as a base for patches, that is by using fats and oils mainly composed of cacao butter, isocacao butter, or triglyceride of a vegetable saturated fatty acid having 12 to 18 carbon atoms as a base together with a penetration enhancer.

Among these bases, cacao butter and isocacao butter are natural vegetable saturated fatty acid triglycerides and the latter fats and oils, i. e., the fats and oils composed of the triglyceride of a vegetable saturated fatty acid of 12 to 18 carbon atoms are semi-synthesized ones. The latter fats and oils are composed of the triglyceride of a vegetable satruated fatty acid such as lauric acid (C 12), myristic acid (C 14), palmitic acid (C 16), and stearic acid (C 18) or a mixture of these triglycerides. They are commercially available as the trade name of "Witepsol" (made by Dinamit Nobel Co.) and can be used as fats and oils for the base in this invention. Suitable commercially available fats and oils are Witepsol H-5, Witepsol H-15, etc.

Thus, according to this invention, there is provided a patch comprising a solution or suspension of a drug component uniformly dispersed in a base mainly comprising a penetration enhancer and fats and oils composed of cacao butter, isocacao butter or the triglyceride of a vegetable saturated fatty acid having 12 to 18 carbon atoms.

DESCRIPTION OF THE PREFERRED EMBODIMENT

Figure 1A:
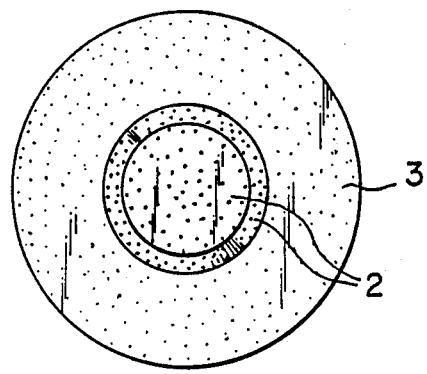
FIG. 1(a) is a plane view showing an example of the construction of a patch of this invention.

Now, as the drug component for the patches of this invention, nicardipine hydrochloride, nifedipine, dipyridamole, formoterol fumarate, indenolol, γ-oryzanol, digoxin, β-methyldigoxin, dimemorfan phosphate, propranolol, etc., can be used. These drug components have hitherto been supplied for treatment as formulations for oral administration and the invention first makes possible the percutaneous administration of these drugs. Bioavailability of drug applied to skin usually is pretty low and hence systemic transdermal formulations are utilized only for limited drugs. Also, since transdermal formulations are used by affixing to the skin, there are restrictions about the kinds and addition amounts of a base to be used and additional component or components from a view point of the maintenance of the form.

The solvent for dissolving or suspending a drug component in this invention, a solvent which can be easily released from the oily base and is compatible with water is fundamentally suitable and examples of the solvent are lactic acid, benzyl alcohol, N-methyl-2-pyrrolidone, crotamiton, glycols (e. g., propylene glycol, ethylene glycol, etc.,), alcohols (e. g., ethanol, isopropanol, etc.,), etc. These solvents may be selectively used solely or as a mixture of them. embodiment of the construction of a patch of this invention.

DESCRIPTION OF THE PREFERRED EMBODIMENT

Now, as the drug component for the patches of this invention, nicardipine hydrochloride, nifedipine, dipyridamole, formoterol fumarate, indenolol, γ-oryzanol, digoxin, β-methyldigoxin, dimemorfan phosphate, propranolol, etc., can be used. These drug components have hitherto been supplied for treatment as formulations for oral administration and the invention first makes possible the percutaneous administration of these drugs. Bioavailability of drug applied to skin usually is pretty low and hence systemic transdermal formulations are utilized only for limited drugs. Also, since transdermal formulations are used by stiking on the skin, there are restrictions about the kinds and addition amounts of a base to be used and additional component or components from a view point of the maintenance of the form.

The solvent for dissolving or suspending a drug component in this invention, a solvent and can be easily released from the oily base and is compatible with water is fundamentally suitable and examples of the solvent are lactic acid, benzyl alcohol, N-methyl-2-pyrrolidone, crotamiton, glycols (e. g., propylene glycol, ethylene glycol, etc.,), alcohols (e. g., ethanol, isopropanol, etc.,), etc. These solvents may be selectively used solely or as a mixture of them.

These solvents are properly selected according to characteristics of the drug component. That is, in the case of using nicardipine hydrochloride, an aqueous urea solution, lactic acid, ethanol, propylene glycol, benzyl alcohol, etc., are properly used as a mixture of them and particularly suitable solvents are a mixed solvent of an aqueous urea solution and lactic acid or propylene glycol and a mixed solvent of an aqueous urea solution, benzyl alcohol, and propylene glycol. Also, a mixed solvent of, for example, N-methyl-2-pyrrolidone and propylene glycol is suitably used for nifedipine, a mixed solvent of, for example, lactic acid, propylene glycol, and an aqueous urea solution for dipyridamole, a mixed solvent of, for example, ethylene glycol and propylene glycol for formoterol fumarate, a solvent such as N-methyl-2-pyrrolidone for γ-oryzanol, and a solvent such as ethylene glycol and propylene glycol for indenolol.

The amount of the solvent for use is the minimum amount capable of dissolving or suspending the drug component and maintaining the form of patch.

As the penetration enhancer, urea, diisopropyl adipate, diethyl adipate, diethyl sebacate, isopropyl myristate, isopropyl palmitate, middle chain fatty acid glyceride, sorbitan middle chain fatty acid ester, etc., can be used. These penetration enhancers can be used solely or as a combination of them. In addition, since propylene glycol which is used as the solvent has also a penetration enhancing action, the above-described penetration enhancer is not necessarily required when it is used as the solvent.

The patches of this invention may further contain, in addition to the above-described components, emulsifiers (e. g., a glycerol monostearic acid ester (Nikkol MGS-B, trade name), polyoxyethylene-hardened castor oil (Nikkol HCO-60, trade name), etc.,), hardening agents (e. g., higher alcohols such as cetyl alcohol, etc.,), oily ointment bases (e. g., white petrolatum etc.,), suspending agents (e. g., silicic anhydride (Aerosil, trade name), etc.,), etc., but fundamentally, the base of an amount capable of maintaining the solid state as the patch form at normal temperature is used.

It is preferred that the patch of this invention is prepared by kneading a solution of drug and the base. That is, the base is melted at a temperature (about 40° C.) necessary for melting the base, a drug solution is gradually added to the molten base while kneading the molten base, and the resultant mixture is kneaded and solidified to provide the patch.

The proportion of each of the patch components of this invention is suitably selected and the amount of the drug component is usually properly determined according to the nature thereof. Also, in general, the amount of the solvent is the smallest necessary amount capable of dissolving or suspending the drug component. The proportion of the base is 60 to 85 w/w %, the proportion of the penetration enhancer is 0.5 to 20 w/w %, preferably 5 to 15 w/w %, and the proportion of other component or components (e. g., an emulsifier, a suspending agent, a preservative, etc.,) is 0.5 to 10 w/w %.

The patch of this invention can be very easily prepared as compared with the above-described conventional patches. Also, the base of the patch of this invention is melted at about body temperature, the patch of this invention is excellent in percutaneous absorption.

Figure 1B:
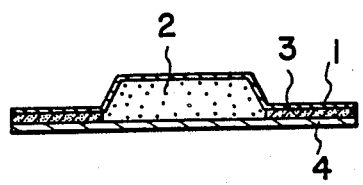
FIG. 1(b) is a cross sectional view thereof.

The construction of the patch of this invention is almost the same as those of conventional patches. FIG. 1 shows a fundamental structure of an example of the patch of this invention, that is, FIG. 1(a) is a plane view showing the construction of an example of the patch of this invention and FIG. 1(b) is a cross sectional view of it. As shown in FIG. 1, patch components 2 are packed in a polyvinyl chloride container 1, an adhesive layer 3 is formed at the portion to be applied to the skin, and the surface of the adhesive layer 3 is covered by a liner 4.

Figure 2:
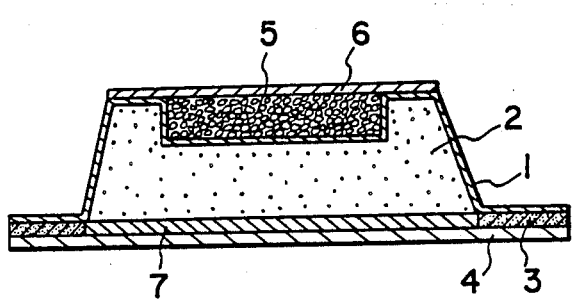
FIG. 2 is a cross sectional view showing another embodiment of the construction of a patch of this invention.

The patch of this invention has the above-described advantages but as another embodiment of the preferred patch of this invention, there is a patch further having a heating element and a filter paper impregnated with propylene glycol. That is, for further improving the form-maintaining property, the patch of this invention sometimes contains a hardening agent such as a higher alcohol (e. g., cetyl alcohol, stearyl alcohol, etc.,), solid paraffin, microcrystalline wax, etc. In this case, however, the melting point range of the patch is liable to become broader and it sometimes happens that the patch does not melt sharply by the body temperature alone. In such a case, the system, as shown in FIG. 2, that a concaved portion is formed at the outer portion (the opposite side to the side to be applied to the skin) of the patch and a heating element 5 is disposed in the concaved portion for heating the patch at the application thereof to the skin can be employed.

For the heating element, a composition mainly composed of an iron powder and generating heat in the presence of oxygen and water is used. The upper portion of the heating element is covered by an aluminum seal 6, etc., and the cover is peeled off prior to use. Also, a propylene glycol-impregnated filter paper 7, for example, Toyo Filter Paper No. 7 (trade name) preliminary impregnated with propylene glycol is disposed between the patch component 2 and a liner 4. By the foregoing construction, the solution of drug dispersed in the oily base of the patch is attracted to the filter paper side at use, whereby the occurence of the molten liquid is prevented and all the surface area of the patch can be effectively utilized.

The following examples will still further illustrate this invention.

EXAMPLE 1

A mixture of 150.5 g of Witepsol H-15 and 5 g of Nikkol MGS-B was melted at about 60° C. and after cooling to about 45° C., the mixture was transferred into a kneader. A solution of 4.5 g of nicardipine hydrochloride dissolved in 40 g of a mixture of benzyl alcohol/propylene glycol/aqueous 50% urea solution (1:1:2, w/w) was gradually added to the mixture and the resultant mixture was kneaded. Then, the mixture was filled in a plastic container made by polyvinyl chloride and solidified by cooling to provide a patch.

EXAMPLE 2

By following the same procedure as Example 1 using Witepsol H-5 in place of Witepsol H-15, a patch was obtained.

EXAMPLE 3

A mixture of 159.1 g of Witepsol H-5 and 9.1 g of Nikkol MGS-B was melted at about 60° C. and after cooling to about 45° C., the mixture was transferred into a kneader. Then, a solution of 4.5 g of nicardipine hydrochloride dissolved in 27.3 g of a mixture of lactic acid/aqueous 50% urea solution (1:2 w/w) was gradually added to the mixture and the resultant mixture was kneaded. The mixture was filled in a plastic container of polyvinyl chloride and solidified by cooling to provide a patch.

EXAMPLE 4

A mixture of 146.4 g of Witepsol H-5 and 9.1 g of Nikkol MGS-B was melted at about 60° C. and after cooling to about 45° C., the mixture was transferred into a kneader. Then, a solution of 4.5 g of nicardipine hydrochloride dissolved in 40 g of a mixture of lactic acid/propylene glycol/aqueous 50% urea solution (1:1:2 w/w) was gradually added to the mixture and the resultant mixture was kneaded. The mixture was filled in a plastic container of polyvinyl chloride and solidified by cooling to provide a patch.

EXAMPLE 5

A mixture of 115.5 g of Witepsol H-5, 10 g of Nikkol MGS-B, 10 g of Nikkol TS-10 (polyoxyethylene sorbitan monostearate), 10 g of Kalcol 60 (trade name, made by Kao Atlas Co., palmityl alcohol) and 10 g of isopropyl myristate was melted at about 60° C. and after cooling to about 45° C., the molten mixture was transferred into a kneader. Thereafter, a solution of 4.5 g of nicardipine hydrochloride dissolved in 40 g of a mixture of benzyl alcohol/propylene glycol/aqueous 50% urea solution (1:1:2 w/w) was gradually added to the mixture and the resultant mixture was kneaded. The mixture was filled in a plastic container of polyvinyl chloride and solidified by cooling to provide a patch.

EXAMPLE 6

A heating element was equipped to the patch in Example 5. As the heating element, Panakairo 25 (trade name, made by Atlas Shoji K. K.) which is composed of iron powder (main component), activated carbon, sodium chloride, etc., was used.

EXAMPLE 7

A mixture of 155 g of Witepsol H-15 and 10 g of Nikkol HCO-60 was melted at about 50° C. and after cooling to about 45° C., the molten mixture was transferred into a kneader. Then, a solution of 5 g of nifedipine dissolved in a mixture of 10 g of N-methyl-2-pyrrolidone, 10 g of propylene glycol, and 10 g of diisopropyl adipate was gradually added to the mixture and the resultant mixture was kneaded. The mixture was filled in a plastic container of polyvinyl chloride and solidified by cooling to provide a patch.

EXAMPLE 8

A mixture of 148.65 g of Witepsol H-5 and 9.1 g of Nikkol MGS-B was melted at about 60° C. and after cooling to about 45° C., the molten mixture was transferred into a kneader. Then, a solution of 2.25 g of dipyridamole dissolved in 40 g of a mixture of latic acid/propylene glycol/aqueous 50% urea solution (1:1:2 w/w) was gradually added to the mixture and the resultant mixture was kneaded. The mixture was filled in a plastic container of polyvinyl chloride and solidified by cooling to provide a patch.

EXAMPLE 9

A mixture of 160 g of Witepsol H-15 and 10 g of Nikkol MGS-B was melted at about 60° C. and after cooling to about 45° C., the molten mixture was transferred into a kneader. Then, a solution of 10 mg of formoterol fumarate dissolved in 30 g of a mixture of ethylene glycol/aqueous 50% urea solution (1:2 w/w) was gradually added to the mixture and the resultant mixture was kneaded. The mixture was filled in a plastic container of polyvinyl chloride and solidified by cooling to provide a patch.

EXAMPLE 10

A mixture of 157.5 g of Witepsol H-15 and 10 g of Nikkol MGS-B was melted at about 60° C. and after cooling to about 45° C., the molten mixture was transferred into a kneader. Then, a solution of 2.5 g of indenolol dissolved in 30 g of a mixture of ethylene glycol/aqueous 50% urea solution (1:2 w/w) was gradually added to the mixture and the resultant mixture was kneaded. The mixture was treated as Example 9 to provide a patch.

EXAMPLE 11

A mixture of 165 g of Witepsol H-5 and 10 g of Nikkol MGS-B was melted at about 60° C. and after cooling to about 45° C., the molten mixture was transferred into a kneader. Then, a solution of 5 g of γ-oryzanol dissolved in 20 g of a mixture of N-methyl-2-pyrrolidone/diisopropyl adipate (1:1 w/w) was gradually added to the solution and the resultant mixture was kneaded. Then, the mixture was treated as Example 10 to provide a patch.

Reference Example

A mixture of 155.5 g of Witepsol H-5, 10 g of Nikkol MGS-B, 10 g of Nikkol IPM (isopropyl myristate), 10 g of Nikkol TS-10 and 10 g of Kalcol 60 was melted and after cooling to about 45° C., the mixture was transferred into a kneader. Then, 4.5 g of nicardipine hydrochloride was added to the mixture followed by kneading and the mixture thus obtained was filled in a plastic container of polyvinyl chloride and solidified to provide a patch.

Percutaneous absorption test in guinea pig

One patch (about 3 g) packed in the plastic container obtained in Example 3, 4, 5 or 6 or Reference Example was applied to the back skin of a guinea pig shaved at the preceding day and five-fold gauzes circularly punched at the center adapting the outer diameter of the plastic container were placed around the plastic container of the patch. The upper surface of the patch thus surrounded by the gauzes was covered by Parafilm and further they were fixed by a surgical tape. After 5 hours since the application of the patch, the blood was collected and the concentration of nicardipine hydrochloride in plasma was measured according to the Higuchi et als' method (*Journal of Chromatography*, 110, 301(1975)). The results thus obtained are shown in the following table.

| Patch | Concentration of nicardipine hydrochloride in plasma |
| --- | --- |
| Example 3 | 54.0 ng/ml |
| Example 4 | 60.7 ng/ml |
| Example 5 | 30.6 ng/ml |
| Example 6 | 51.5 ng/ml |
| Reference Example | 5.6 ng/ml |

What is claimed is:

1. A transdermal patch comprised of a polyvinyl chloride container, an adhesive layer on said container at the portion to be applied to the skin, and wherein said adhesive layer is covered by a liner, said patch containing a solution or a suspension of a drug component selected from the group consisting of nicardipine hydrochloride, nifedipine, dipyridamole, formoterol fumarate, indenolol and -oryzanol, and wherein said drug component is uniformly dispersed in a base mainly comprising cacao butter, isocacao butter or a triglyceride of a vegetable saturated fatty acid having 12 to 18 carbon atoms together with a penetration enhancer.

2. The patch as claimed in claim 1, wherein the base is fats and oils comprising a triglyceride of a vegetable saturated fatty acid having 12 to 18 carbon atoms.

3. The patch as claimed in claim 1, wherein the solution of the drug component is a solution of nicardipine hydrochloride dissolved in a mixed solvent of an aqueous urea solution, lactic acid and propylene glycol.

4. The patch as claimed in claim 1, wherein the solution of the drug component is a solution of dipyridamole dissolved in a mixed solvent of an aqueous urea solution, lactic acid and propylene glycol.

5. The patch as claimed in claim 1, wherein the solution of the drug component is a solution of nicardipine hydrochloride dissolved in a mixed solvent of an aqueous urea solution, benzyl alcohol, and propylene glycol.

6. The patch as claimed in claim 1, 4, 5 or 6, wherein a propylene glycol-impregnated filter paper is disposed at the side of the patch to be applied to the skin.

7. A transdermal patch comprised of a container, an adhesive layer on said container at the portion to be applied to the skin, and said container and surface of the adhesive layer covered by a liner and contained within said container a solution or a suspension of a drug component selected from the group consisting of nicardipine hydrochloride, nifedipine, dipyridamole, formoterol fumarate, indenolol and γ-oryzanol, and wherein said drug component is uniformly dispersed in a base mainly comprising cacao butter, isocacao butter or a triglyceride of a vegetable saturated fatty acid having 12 to 18 carbon atoms together with a penetration enhancer.

* * * * *